United States Patent [19]

Swithenbank

[11] Patent Number: 4,913,729
[45] Date of Patent: Apr. 3, 1990

[54] HERBICIDAL 4-TRIFLUOROMETHYL-3'-SUBSTITUTED AMINE-4'-NITRO DIPHENYL ETHERS

[75] Inventor: Colin Swithenbank, Perkasie, Pa.

[73] Assignee: Rohm and Haas Company, Philadelphia, Pa.

[21] Appl. No.: 57,674

[22] Filed: Jun. 3, 1987

Related U.S. Application Data

[63] Continuation of Ser. No. 544,050, Oct. 24, 1983, which is a continuation-in-part of Ser. No. 312,453, Oct. 19, 1981, Pat. No. 4,419,124.

[51] Int. Cl.$^4$ ............................................. A01N 37/34
[52] U.S. Cl. ........................................ 71/105; 71/107; 71/115; 71/121; 558/414; 558/424; 560/21; 562/435; 564/430
[58] Field of Search ................. 711/98, 105, 115, 121, 711/107; 562/435; 504/430; 558/414, 424

[56] References Cited

U.S. PATENT DOCUMENTS

| | | | |
|---|---|---|---|
| 3,013,054 | 12/1961 | Richter | 71/98 |
| 3,928,416 | 12/1975 | Bayer et al. | 71/98 |
| 3,979,437 | 9/1976 | Theissen | 71/98 |
| 4,046,798 | 9/1977 | Bayer et al. | 71/98 |
| 4,063,929 | 12/1977 | Bayer et al. | 71/98 |
| 4,164,409 | 8/1979 | Theissen | 71/98 |
| 4,364,875 | 12/1982 | Sehring et al. | 564/430 |

FOREIGN PATENT DOCUMENTS

| | | | |
|---|---|---|---|
| 2938595 | of 0000 | Fed. Rep. of Germany | 71/98 |
| 1502538 | of 0000 | France | 71/98 |
| 2105715 | of 0000 | United Kingdom | 71/98 |

OTHER PUBLICATIONS

Central Patents Index, Section C: AgDoc 48892 E/24 (J57072-946), Derwent Publications Ltd. (1982).
Central Patents Index, Section C: AgDoc 56698 K/24 (EP 80-746), Derwent Publications Ltd.

*Primary Examiner*—James H. Reamer
*Attorney, Agent, or Firm*—Barbara V. Maurer; Polly E. Ramstad; Douglas Winters

[57] ABSTRACT

The herbicidal 4-trifluoromethyl-3'-substituted amino-4'-nitro diphenyl ethers comprise a class of compounds that are highly effective herbicides.

16 Claims, No Drawings

HERBICIDAL 4-TRIFLUOROMETHYL-3'-SUBSTITUTED AMINE-4'-NITRO DIPHENYL ETHERS

CROSS REFERENCE TO RELATED APPLICATIONS

This application is a continuation, of application Ser. No. 544,050, filed on October 24, 1983 which is a continuation-in-part of Ser. No. 312,453, filed October 19, 1981, now U.S. Pat. No. 4,419,124 issued December 6, 1983.

BACKGROUND OF THE INVENTION

1. Field of the Invention

This invention is concerned with substituted diphenyl ethers and their use as herbicides.

2. Description of the Prior Art

It has been proposed to use as herbicides 2-methoxybenzoic acids (U.S. Pat. No. 3,013,054) and 4-phenoxybenzoic acids (French Pat. No. 1,502,538) substituted phenoxybenzoic acids (U.S. Pat. Nos. 3,979,437 and 4,164,409) and certain 4-trifluoromethyl-4'-nitrodiphenyl ethers (U.S. Pat. Nos. 3,928,416, 4,046,798, and 4,063,929). It is the discovery of this invention, however, that certain 4-trifluoromethyl-3'-nitrogen-substituted-4'-substituted diphenyl ethers are very effective herbicides.

DESCRIPTION OF THE INVENTION

This invention provides herbicidal compounds of the formula:

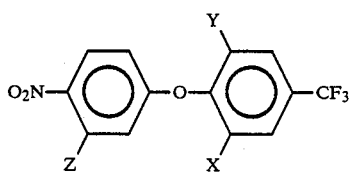

(I)

wherein
X is a hydrogen, fluoro, chloro, bromo, trifluoromethyl or cyano group;
Y is a hydrogen, fluoro, chloro or bromo atom; and
Z is NH—$R^1$-$R^2$ wherein $R^1$ is a ($C_1$-$C_5$)alkylene and $R^2$ is a hydroxy, carb($C_1$-$C_4$)alkoxy (—COOR), carboxy (—COOH) or an agronomically acceptable salt thereof or a cyano group.

When $R^1$ is a ($C_2$-$C_5$)alkylene it may be substituted with methyl groups.

Preferred compounds of the invention are those where X is a fluoro, chloro or cyano group; Y is a hydrogen, fluoro or chloro atom; $R^1$ is a ($C_2$-$C_5$)alkylene which may be optionally substituted with up to one methyl group per carbon atom; and $R^2$ is a carb($C_1$-$C_4$)alkoxy group.

More preferred compounds of the invention are those where X is a chloro or fluoro atom; Y is a hydrogen; $R^1$ is a ($C_2$-$C_3$)alkylene which may be optionally substituted with up to one methyl group per carbon atom of the alkylene group or a ($C_4$-$C_5$)alkylene which is substituted with at least one methyl group and optionally substituted with additional methyl groups up to one per carbon atom of the alkylene group; and $R^2$ is a carb(-$C_1$-$C_4$)alkoxy group.

When the Z substituent contains a carboxy group, either the free acid or an agronomically acceptable salt form can be used, preferably an alkali metal salt, most preferably sodium or potassium, or an alkaline earth metal salt.

Examples of the compounds of the invention embraced by Formula I include those compounds of formula I wherein:

| X | Y | Z |
|---|---|---|
| H | H | $NHCH_2CH_2OH$ |
| Cl | Cl | $NHCH_2CH_2CO_2H$ |
| F | H | $NHCH_2CH_2CH_2CO_2CH_3$ |
| Br | Br | $NHCH_2CH_2CH_2CN$ |
| $CF_3$ | H | $NHCH_2CH_2CH_2CH_2CO_2CH_2CH_3$ |
| CN | H | $NHCH_2CH_2CH_2CH_2CH_2CO_2CH_3$ |
| H | H | $NHCH_2CH_2CH_2CH_2CO_2CH_2CH_3$ |
| Cl | Br | $NHCH_2CH_2CO_2H$ |
| F | Br | $NHCH_2CH_2CO_2CH_3$ |
| Br | H | $NHCH_2CH_2CO_2H$ |
| $CF_3$ | H | $NHCH_2CH_2CO_2CH_3$ |
| CN | Cl | $NHCH_2CH_2CO_2CH_3$ |
| H | H | $NHCH_2CH(CH_3)CO_2CH_3$ |
| Cl | H | $NHCH_2CH(CH_3)CO_2CH_3$ |
| F | H | $NHCH(CH_3)CH_2CO_2CH_3$ |
| Br | H | $NHCH_2C(CH_3)_2CO_2CH_3$ |
| $CF_3$ | H | $NHCH(CH_3)CH_2CO_2CH_2CH_3$ |
| CN | H | $NHCH_2CO_2CH_3$ |
| Cl | H | $NHCH_2CH(CH_3)CO_2Na$ |
| Cl | H | $NHCHCHCO_2CH_3$ |

In addition to the foregoing, the invention embraces each of the specific compounds of the same general structures wherein the "Z" moiety (Formula I) is replaced by the following:

| | |
|---|---|
| —$NHC(=CH_2)CO_2CH_2CH_3$ | —$NHCH(CH_3)CO_2CH_2CH_3$ |
| —$N=C(Cl)CO_2CH_2CH_3$ | —$NHC(CH_3)=CHCO_2CH_2CH_3$ |
| —$NHCH_2CN$ | —$NHCH_2CO_2CH_3$ |
| —$NHCH_2CH_2CO_2CH_3$ | —$NHCH_2CH_2CH_2CO_2CH_3$ |
| —$N=C(CH_3)CN$ | —$N=C(CH_3)CO_2CH_3$ |
| —$NHC(=O)CO_2CH_3$ | —$NHCH_2CH_2CN$ |
| —$NHCH_2CH_2CH_2CO_2H$ | |

Preferred compounds of the invention include those wherein X is a chloro atom, Y is a hydrogen atom and Z is:

| | |
|---|---|
| $NHCH(CH_3)CH_2CH_2CO_2CH_3$ | $NHCH_2CH_2CO_2CH_3$ |
| $NHCH_2CH(CH_3)CH_2CO_2CH_3$ | $NHCH_2CH_2CO_2CH_2CH_3$ |
| $NHCH_2CH_2CH(CH_3)CO_2CH_2CH_3$ | $NHCH(CH_3)CH_2CO_2CH_3$ |
| $NHCH_2CH_2CN$ | $NHCH(CH_3)CH_2CO_2CH_2CH_3$ |
| $NHCH_2(CH_3)CH_2CN$ | $NHCH(CH_3)CH_2CO_2CH(CH_3)_2$ |
| $NH(CH_2)_3CO_2CH_3$ | $NHCH_2CH(CH_3)CO_2CH_3$ |
| $NH(CH_2)_4CO_2CH_3$ | $NHCH_2CH(CH_3)CO_2CH_2CH_3$ |
| $NH(CH_2)_5CO_2CH_2CH_3$ | $NHCH(CH_3)CH(CH_3)CH(CH_3)CO_2Me$ |

More preferred compounds of the invention include methyl-3-[5-(2-chloro-4-(trifluoromethyl)phenoxy)-2-nitrophenylamino]butyrate, methyl-3-[5-(2-chloro-4-trifluoromethyl)phenoxy) 2-nitro-phenylamino]propionate and, most preferably, ethyl-3-[5-(2-chloro-4-(trifluoromethyl)-phenoxy)-2-nitro-phenylamino]propionate.

The novel diphenyl ethers of the invention are useful both as preemergence and as postemergence herbicides. Preemergence herbicides are ordinarily used to treat the soil in which the desired crop is to be planted by application either before seeding, during seeding, or, as in most applications, after seeding and before the crop emerges. Post-emergence herbicides are those which are applied after the plants have emerged and during their growth period.

Among the crops on which the diphenyl ethers of the invention can be advantageously employed are, for example, cotton, soybeans, peanuts, safflower, beans, peas, carrots, corn, wheat, and other cereal crops.

Diphenyl ethers of the invention are useful for controlling weeds in rice crops. When used in transplanted rice crops, the ethers can be applied either preemergence or post-emergence to the weeds—that is, they can be applied to the growth medium of the transplanted plants either before the weed plants have emerged or while they are in their early stages of growth. The ethers can be applied to the growth medium either before or after the rice has been transplanted to that medium.

The diphenyl ethers of the invention can be applied in any amount which will give the required control of weeds. A preferred rate of application of the herbicides of the invention is from about 0.1 to about 12, and most preferably about 0.25 to 4, pounds of the diphenyl ether per acre.

Under some conditions, the diphenyl ethers of the invention may be advantageously incorporated into the soil or other growth medium prior to planting a crop. This incorporation can be carried out by any convenient means, including by simple mixing with the soil, by applying the diphenyl ether to the surface of the soil and then disking or dragging into the soil to the desired depth, or by employing a liquid carrier to accomplish the necessary penetration and impregnation.

A diphenyl ether of the invention can be applied to the growth medium or to plants to be treated either by itself or, as is generally done, as a component in a herbicidal composition or formulation which also comprises an agronomically acceptable carrier. By agronomically acceptable carrier is meant any substance which can be used to dissolve, disperse, or diffuse a herbicidal compound in the composition without impairing the effectiveness of the herbicidal compound and which by itself has no detrimental effect on the soil, equipment, crops, or agronomic environment. Mixtures of the diphenyl ethers of the invention may also be used in any of these herbicidal formulations. The herbicidal compositions of the invention can be either solid or liquid formulations or solutions. For example, the diphenyl ethers can be formulated as wettable powders, emulsifiable concentrates, dusts, granular formulations, aerosols, or flowable emulsion concentrates. In such formulations, the compounds are extended with a liquid or solid carrier and, when desired, suitable surfactants are incorporated.

It is usually desirable, particularly in postemergence applications, to include adjuvants, such as wetting agents, spreading agents, dispersing agents, stickers, adhesives, and the like, in accordance with agricultural practices. Examples of adjuvants which are commonly used in the art can be found in the John W. McCutcheon, Inc. publication "Detergents and Emulsifiers Annual".

The diphenyl ether compounds of this invention can be dissolved in any appropriate solvent. Examples of solvents which are useful in the practice of this invention include alcohols, ketones, aromatic hydrocarbons, halogenated hydrocarbons, dimethylformamide, dioxane, dimethyl sulfoxide, and the like. Mixtures of these solvents can also be used. The concentration of the solution can vary from about 2% to about 98% with a preferred range being about 25% to about 75%.

For the preparation of emulsifiable concentrates, the diphenyl ether can be dissolved in organic solvents, such as benzene, toluene, xylene, methylated naphthalene, corn oil, pine oil, o-dichlorobenzene, isophorone, cyclohexanone, methyl oleate, and the like, or in mixtures of these solvents, together with an emulsifying agent which permits dispersion in water. Suitable emulsifiers include, for example, the ethylene oxide derivatives of alkylphenols or long-chain alcohols, mercaptans, carboxylic acids, and reactive amines and partially esterified polyhydric alcohols. Solvent-soluble sulfates or sulfonates, such as the alkaline earth salts or amine salts of alkylbenzenesulfonates and the fatty alcohol sodium sulfates, having surface-active properties can be used as emulsifiers either alone or in conjunction with an ethylene oxide reaction product. Flowable emulsion concentrates are formulated similarly to the emulsifiable concentrates and include, in addition to the above components, water and a stabilizing agent such as a water-soluble cellulose derivative or a water-soluble salt of a polyacrylic acid. The concentration of the active ingredient in emulsifiable concentrates is usually about 10% to 60% and in flowable emulsion concentrates, this can be as high as about 75%.

Wettable powders suitable for spraying, can be prepared by admixing the compound with a finely divided solid, such as clays, inorganic silicates and carbonates, and silicas and incorporating wetting agents, sticking agents, and/or dispersing agents in such mixtures. The concentration of active ingredients in such formulations is usually in the range of about 20% to 98%, preferably about 40% to 75%. A dispersing agent can constitute about 0.5% to about 3% of the composition, and a wetting agent can constitute from about 0.1% to about 5% of the composition.

Dusts can be prepared by mixing the compounds of the invention with finely divided inert solids which may be organic or inorganic in nature. Materials useful for this purpose include, for example, botanical flours, silicas, silicates, carbonates and clays. One convenient method of preparing a dust is to dilute a wettable powder with a finely divided carrier. Dust concentrates containing about 20% to 80% of the active ingredient are commonly made and are subsequently diluted to about 1% to 10% use concentration.

Granular formulations can be prepared by impregnating a solid such as granular fuller's earth, vermiculite, ground corn cobs, seed hulls, including bran or other grain-hulls, or similar material. A solution of one or more of the diphenyl ethers in a volatile organic solvent can be sprayed or mixed with the granular solid and the solvent then removed by evaporation. The granular material can have any suitable size, with a preferable size range of 16 to 60 mesh. The diphenyl ether will usually comprise about 2 to 15% of the granular formulation.

The diphenyl ethers of the invention can also be mixed with fertilizers or fertilizing materials before their application. In one type of solid fertilizing composition in which the diphenyl ethers can be used, particles of a fertilizer or fertilizing ingredients, such as ammonium sulfate, ammonium nitrate, or ammonium phosphate, can be coated with one or more of the ethers. The solid diphenyl ethers and solid fertilizing material can also be admixed in mixing or blending equipment, or they can be incorporated with fertilizers in granular formulations. Any relative proportion of diphenyl ether and fertilizer can be used which is suitable for the crops and weeds to be treated. The diphenyl ether will commonly be from about 5% to about 25% of the fertilizing composition. These compositions provide fertilizing materials which promote the rapid growth of desired plants, and at the same time control the growth of undesired plants.

The diphenyl ethers of the invention can be applied as herbicidal sprays by methods commonly employed, such as conventional high-gallonage hydraulic sprays, low gallonage sprays, airblast spray, aerial sprays and dusts. For low volume applications a solution of the compound is usually used. The dilution and rate of application will usually depend upon such factors as the type of equipment employed, the method of application, the area to be treated and the type and stage of development of the weeds.

For some applications, it may be desirable to add one or more other herbicides along with diphenyl ethers of the invention. Examples of other herbicides which can be incorporated to provide additional advantages and effectiveness include:

CARBOXYLIC ACIDS AND DERIVATIVES 2,3,6-trichlorobenzoic acid and its salts
2,3,5,6-tetrachlorobenzoic acid and its salts
2-methoxy-3,5,6-trichlorobenzoic acid and its salts
2-methoxy-3,6-dichlorobenzoic acid and its salts
2-methyl-3,6-dichlorobenzoic acid and its salts
2,3-dichloro-6-methylbenzoic acid and its salts
2,4-dichlorophenoxyacetic acid and its salts and esters
2,4,5-trichlorophenoxyacetic acid and its salts and esters
2-methyl-4-chlorophenoxyacetic acid and its salts and esters
2-(2,4,5-trichlorophenoxy)propionic acid and its salts and esters
4-(2,4-dichlorophenoxy)butyric acid and its salts and esters
4-(2-methyl-4-chlorophenoxy)butyric acid and its salts and esters
2,3,6-trichlorophenylacetic acid and its salts
3,6-endoxohexahydrophthalic acid
dimethyl 2,3,5,6-tetrachloroterephthalate
trichloroacetic acid and its salts
2,2-dichloropropionic acid and its salts
2,3-dichloroisobutyric acid and its salts

CARBAMIC ACID DERIVATIVES ethyl N,N-di(n-propyl)thiolcarbamate
propyl N,N-di(n-propyl)thiolcarbamate
ethyl N-ethyl-N-(n-butyl)thiolcarbamate
propyl N-ethyl-N-(n-butyl)thiolcarbamate
2-chloroallyl N,N-diethyldithiocarbamate
N-methyldithiocarbamic acid salts
ethyl 1-hexamethyleneiminecarbothiolate
isopropyl N-phenylcarbamate
isopropyl N-(m-chlorophenyl)carbamate
4-chloro-2-butynyl N-(m-chlorophenyl)carbamate
methyl N-(3,4-dichlorophenyl)carbamate

PHENOLS dinitro-o-(sec-butyl)phenol and its salts
pentachlorophenol and its salts

SUBSTITUTED UREAS 3-(3,4-dichlorophenyl)-1,1-dimethylurea
3-phenyl-1,1-dimethylurea
3-(3,4-dichlorophenyl)-3-methoxy-1,1-dimethylurea
3-(4-chlorophenyl)-3-methoxy-1,1-dimethylurea
3-(3,4-dichlorophenyl)-1-n-butyl-1-methylurea
3-(3,4-dichlorophenyl)-1-methoxy-1-methylurea
3-(4-chlorophenyl)-1-methoxy-1-methylurea
3-(3,4-dichlorophenyl)-1,1,3-trimethylurea
3-(3,4-dichlorophenyl)-1,1-diethylurea
dichloral urea

SUBSTITUTED TRIAZINES 2-chloro-4,6-bis(ethylamino)-s-triazine
2-chloro-4-ethylamino-6-isopropylamino-s-triazine
2-chloro-4,6-bis(methoxypropylamino)-s-triazine
2-methoxy-4,6-bis(isopropylamino)-s-triazine
2-chloro-4-ethylamino-6-(3-methoxypropylamino)-s-triazine
2-methylmercapto-4,6-bis(isopropylamino)-s-triazine
2-methylmercapto-4,6-bis(ethylamino)-s-triazine
2-methylmercapto-4-ethylamino-6-isopropylamino-s-triazine
2-chloro-4,6-bis(isopropylamino)-s-triazine
2-methoxy-4,6-bis(ethylamino)-s-triazine
2-methoxy-4-ethylamino-6-isopropylamino-s-triazine
2-methylmercapto-4-(2-methoxyethylamino)-6-isopropylamino-s-triazine

DIPHENYL ETHER DERIVATIVES 2,4-dichloro-4'-nitrodiphenyl ether
2,4,6-trichloro-4'-nitrodiphenyl ether
2,4-dichloro-6-fluoro-4'-nitrodiphenyl ether
3-methyl-4'-nitrodiphenyl ether
3,5-dimethyl-4'-nitrodiphenyl ether
2,4'-dinitro-4-trifluoromethyldiphenyl ether
2,4-dichloro-3'-methoxy-4'-nitrodiphenyl ether

ANILIDES

N-(3,4-dichlorophenyl)propionamide
N-(3,4-dichlorophenyl)methacrylamide
N-(3-chloro-4-methylphenyl)-2-methylpentanamide
N-(3,4-dichlorophenyl)trimethylacetamide
N-(3,4-dichlorophenyl)-α,α-dimethylvaleramide
N-isopropyl-N-phenylchloroacetamide
N-n-butoxymethyl-N-(2,6-diethylphenyl)chloroacetamide
N-n-methoxymethyl-N-(2,6-diethylphenyl)chloroacetamide

URACILS 5-bromo-3-s-butyl-6-methyluracil
5-bromo-3-cyclohexyl-1,6-dimethyluracil
3-cyclohexyl-5,6-trimethyleneuracil
5-bromo-3-isopropyl-6-methyluracil
3-tert-butyl-5-chloro-6-methyluracil

NITRILES 2,6-dichlorobenzonitrile
diphenylacetonitrile
3,5-dibromo-4-hydroxybenzonitrile
3,5-diiodo-4-hydroxybenzonitrile

OTHER ORGANIC HERBICIDES 2-chloro-N,N-diallylacetamide
N-(1,1-dimethyl-2-propynyl)-3,5-dichlorobenzamide
maleic hydrazide
3-amino-1,2,4-triazole
monosodium methanearsonate
disodium methanearsonate
N,N-dimethyl-α,α-diphenylacetamide N,N-di(n-propyl)-2,6-dinitro-4-trifluoromethylaniline
N,N-di(n-propyl)-2,6-dinitro-4-methylaniline
N,N-di(n-propyl)-2,6-dinitro-4-methylsulfonylaniline
O-(2,4-dichlorophenyl)-O-methyl-isopropylphosphoramidothioate
4-amino-3,5,6-trichloropicolinic acid
2,3-dichloro-1,4-naphthoquinone
di(methoxythiocarbonyl)disulfide
3-isopropyl-1H-2,1,3-benzothiadiazin-(4)3H-one-2,2-dioxide
6,7-dihydrodipyridol[1,2-a:2',1'-c]pyrazidinium salts
1,1'-dimethyl-4,4'-bipyridinium salts
3,4,5,6-tetrahydro-3,5-dimethyl-2-thio-2H-1,3,5-thiadiazine.

When mixtures of herbicides are employed, the relative proportions which are used will depend upon the crop to be treated and the degree of selectivity in weed control which is desired.

The diphenyl ethers of the invention or their precursors can be prepared by reacting a suitably substituted phenol, or the potassium or sodium salt of the phenol, with a suitably substituted halobenzene, such as a chloro-or fluorobenzene, in the presence of an alkaline agent or in the Ullman ether synthesis. They can be prepared by other conventional techniques. For example, by the nucleophilic displacement of a nitro group of an appropriately substituted 4-(4-trifluoromethylphenoxy)-1,2-dinitrobenzene, e.g., 4-(2-chloro-4-trifluoroethylphenoxy)-1,2-dinitrobenzene, by an amine hydrochloride:

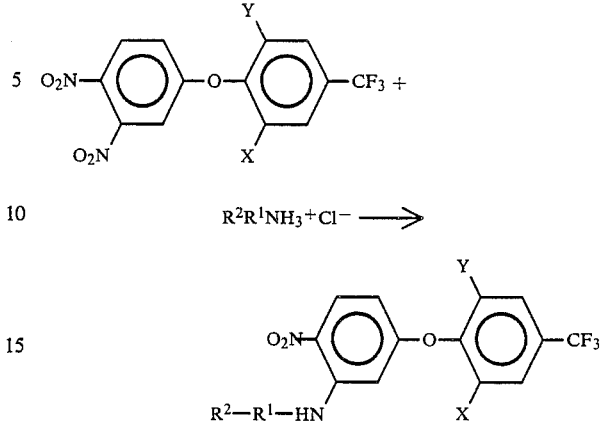

The appropriately substituted diphenylamines and amine hydrochlorides can be prepared by procedures described in the literature or are commercially available materials.

The reaction can be conducted in the presence of a polar solvent, such as dioxane, ethanol and dimethylsufoxide, at a temperature of from about 25° to about 150° C. and preferably from about 25° to 120° C.

The following examples will further illustrate this invention but are not intended to limit it in any way. In Table I typicaly diphenyl ethers of the invention are listed with their melting points and elemental analyses. Specific, illustrative preparations of the compounds are described after Table I.

TABLE 1

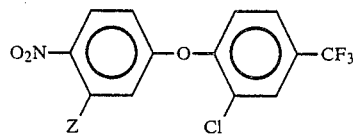

| Example No. | Z | MP °C. | Composition | Element | Cal'd. | Found |
|---|---|---|---|---|---|---|
| 1 | NHCH$_2$CH$_2$CO$_2$Et | 89–89.5 | C$_{18}$H$_{16}$ClF$_3$N$_2$O$_5$ | C | 49.95 | 49.68 |
| | | | | H | 3.73 | 3.63 |
| | | | | N | 6.47 | 6.41 |
| | | | | Cl | 8.19 | 8.10 |
| | | | | F | 13.17 | 13.17 |
| 2 | NHCH$_2$CH$_2$CH$_2$CO$_2$H | oil | C$_{17}$H$_{14}$ClF$_3$N$_2$O$_5$ | C | 48.76 | 49.99 |
| | | | | H | 3.37 | 3.72 |
| | | | | N | 6.69 | 6.45 |
| | | | | Cl | 8.47 | 8.42 |
| | | | | F | 13.61 | 13.07 |
| 3 | NHCH$_2$CH$_2$CN | 118–121 | C$_{16}$H$_{11}$ClF$_3$N$_3$O$_3$ | C | 49.82 | 49.53 |
| | | | | H | 2.87 | 2.89 |
| | | | | N | 10.89 | 11.03 |
| | | | | Cl | 9.19 | 9.24 |
| | | | | F | 14.78 | 14.34 |
| 4 | NHCH$_2$CH$_2$CH$_2$CO$_2$Et | oil | C$_{19}$H$_{18}$ClF$_3$N$_2$O$_5$ | C | 51.07 | 50.80 |
| | | | | H | 4.06 | 3.83 |
| | | | | N | 6.27 | 6.35 |
| | | | | Cl | 7.94 | 8.08 |
| | | | | F | 12.76 | 12.54 |
| 5 | NHCH$_2$CH$_2$CO$_2$CH$_3$ | 78–82 | C$_{17}$H$_{14}$ClF$_3$N$_2$O$_5$ | C | 48.76 | 48.66 |
| | | | | H | 3.37 | 3.68 |
| | | | | N | 6.69 | 6.80 |
| | | | | Cl | 8.47 | 7.85 |
| | | | | F | 13.61 | 12.85 |
| 6 | NHCH$_2$CH$_2$CO$_2$H | 80 | C$_{16}$H$_{12}$ClF$_3$N$_2$O$_5$ | C | 47.48 | 44.78 |
| | | | | H | 2.99 | 3.10 |
| | | | | N | 6.92 | 6.97 |
| | | | | Cl | 8.22 | 8.22 |
| | | | | F | 14.08 | 10.67 |
| 7 | NHCH$_2$CH$_2$CH$_2$CO$_2$Me | 45–50 | C$_{17}$H$_{16}$ClF$_3$N$_2$O$_5$ | C | 48.76 | 49.91 |

TABLE 1-continued

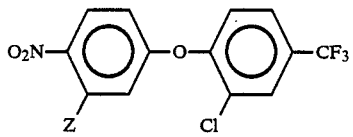

| Example No. | Z | MP °C. | Composition | Element | Cal'd. | Found |
|---|---|---|---|---|---|---|
| | | | | H | 3.37 | 3.68 |
| | | | | N | 6.69 | 6.50 |
| | | | | Cl | 8.47 | 8.74 |
| | | | | F | 13.61 | 14.09 |
| 8 | NHCH$_2$CN | 89–90 | C$_{15}$H$_9$ClF$_3$N$_3$O$_5$ | C | 48.5 | 48.70 |
| | | | | H | 2.4 | 2.69 |
| | | | | N | 11.3 | 9.53 |
| | | | | Cl | 9.5 | 9.50 |
| | | | | F | 15.3 | 14.92 |
| 9 | NHCH$_2$CH$_2$CH$_2$CO$_2$K | — | C$_{17}$H$_{13}$ClF$_3$KN$_2$O$_5$ | | | |
| 10 | NHCH(Me)CH$_2$CO$_2$Me | 74–77 | C$_{18}$H$_{16}$ClF$_3$N$_2$O$_5$ | C | 49.95 | 49.66 |
| | | | | H | 3.73 | 3.68 |
| | | | | N | 6.47 | 6.49 |
| | | | | Cl | 8.19 | 8.35 |
| | | | | F | 13.17 | 13.85 |
| 11 | NHCH$_2$CH(Me)CO$_2$Me | oil | C$_{18}$H$_{16}$ClF$_3$N$_2$O$_5$ | C | 49.95 | 49.44 |
| | | | | H | 3.73 | 3.52 |
| | | | | N | 6.47 | 6.50 |
| | | | | Cl | 8.19 | 8.25 |
| | | | | F | 13.17 | 13.44 |
| 12 | NHCH$_2$CH$_2$CO$_2$CH(Me)$_2$ | 90–91 | C$_{19}$H$_{18}$ClF$_3$N$_2$O$_5$ | C | 51.1 | 50.29 |
| | | | | H | 4.1 | 4.16 |
| | | | | N | 6.3 | 6.12 |
| | | | | Cl | 7.9 | 7.46 |
| | | | | F | 12.8 | 12.73 |
| 13 | NH(CH$_2$)$_5$CO$_2$Me | 60–62 | C$_{20}$H$_{20}$ClF$_3$N$_2$O$_5$ | C | 52.1 | 52.82 |
| | | | | H | 4.4 | 4.42 |
| | | | | N | 6.1 | 6.28 |
| | | | | Cl | 7.7 | 7.80 |
| | | | | F | 12.4 | 12.78 |
| 14 | NHCH$_2$CH$_2$CO$_2$K | dec 180–190 | C$_{16}$H$_{11}$ClF$_3$KN$_2$O$_3$ | C | 43.4 | 40.12 |
| | | | | H | 2.5 | 2.84 |
| | | | | N | 6.4 | 6.13 |
| | | | | Cl | 8.0 | 7.39 |
| | | | | F | 12.9 | 9.53 |

EXAMPLE 1:

Preparation of Ethyl-3-(5-(2-chloro-4-(trifluoromethyl)phenoxy)-2-nitro-phenylamino)propionate To a mixture of ethyl 3-aminopropionate hydrochloride (10.29 gm, 0.067 mol), 4-(2-chloro-4-(trifluoromethyl)phenoxy)-1,2-dinitrobenzene (5.96 gm, 0.016 mol) and 150 ml of dry dioxane there was added 9.12 gm (0.066 mol) of anhydrous potassium carbonate. The mixture was stirred at room temperature for about 48 hours. The resultant bright-yellow suspension was poured into water and extracted with ether. The etheral solution was then washed with saturated sodium chloride and dried over anhydrous magnesium sulfate. Filtration and evaporation of the filtrate gave an orange oil which, when mixed with methanol yielded orange crystals which were isolated by filtration and dried to give the desired product.

EXAMPLE 3:

Preparations of 3-[5-(2-chloro-4-(trifluoromethyl)-2-nitro-phenylamino]propionitrile A solution of 3-aminopropionitrile (5.14 gm, 0.073 mol), 4-(2-chloro-4-(trifluoromethyl)phenoxy)-1,2-dinitrobenzene (6.2 gm, 0.017 mol) in 50 ml of dry dioxane was stirred about 12 hours at room temperature, then heated at reflux for about 8 hours. Upon cooling, the brilliant yellow suspension was poured into water. The mixture was extracted several times with ether. The combined ethereal extracts were washed with saturated sodium chloride solution, dried over anhydrous magnesium sulfate, filtered and evaporated under reduced pressure to yield 7.2 gm of the desired product.

EXAMPLE 5:

Preparation of Methyl-3-(5-(2-chloro-4-(trifluoromethyl)phenoxy)-2-nitro-phenylamino)propionate In a flask equipped with a reflux condenser, magnetic stirrer, nitrogen inlet and heating mantle, 4-(2-chloro-4-(trifluoromethyl)phenoxy-1,2-dinitrobenzene (6.70 gm, 18.5 mmol), powdered potassium carbonate (9.7 gm, 70 mmol), beta-alanine, methyl ester hydrochloride (10 gm, 71.6 mmol) and 100 ml dioxane were combined and heated to reflux. After 3 hours, the bright yellow suspension was diluted with water, extracted with ether. The combined organic extracts were shaken with brine, dried (MgSO$_4$), filtered, concentrated and triturated with methanol to yield 7 gm of orange crystals.

EXAMPLE 7:

Preparation of Methyl-4-(5-(2-chloro-4-(trifluoromethyl)phenoxy)-2-nitro-phenylamino)butyrate To a suspension of 3-[5-(2-chloro-4-(trifluoromethyl)-phenoxy)-2-nitrophenylamino]butyric acid (2.50 gm, 5.97 mmol) in 50 ml toluene cooled to 0° C. was added triethylamine (0.83 ml, 5.97 mmol). Methyl chloroformate (0.51 ml, 6.57 mmol) was added. After 1 hour the reaction was warmed to room temperature, an excess of methanol was added and the mixture was allowed to stir overnight. The reaction mixture was diluted with water, ether extracted, shaken with brine and dried (MgSO4) filtered and concentrated under vacuum. The resulting viscous oil was purified by column chromatography, silica gel, 40% ether/hexane to afford 2 gm of the desired product.

EXAMPLE 8:

Preparation of 2-[5-(2-chloro-4-(trifluoromethyl)phenoxy)-2-nitro-phenylamino]acetonitrile Into a flask equipped with a reflux condenser, magnetic stirrer, nitrogen inlet and heating mantle, there was added 4-(2-chloro-4-(trifluoromethyl)-phenoxy)-1,2-dinitrobenzene (5 gm, 0.014 mol), aminoacetonitrile hydrochloride (5.1 gm, 0.055 mol), anhydrous potassium carbonate (7.4 gm, 0.053 formula weight) and 50 ml of dioxane. The solution was sirred and refluxed overnight, cooled and poured into water. Following ether extraction, the organic layer was dried and evaporated to a residue. The residual material was chromatographed over silica gel using 15% acetone and 85% hexane as the eluant to yield 800 mg of the desired product.

EXAMPLE 9 and 14:

Preparations of Potassium-4-(5-(2-chloro-4-(trifluoromethyl)phenoxy)-2-nitro-phenylamino)butyrate and potassium-3-(5-(2-chloro-4-(trifluoromethyl)phenoxy)-2-nitro-phenylamino)propionate The diphenyl ether amino acid ester, i.e., compounds of examples 1 and 4 (about 0.02 mole), respectively, was dissolved in a solution of about 1 gm (about 0.02 mole) of potassium hydroxide in about 70 mls of absolute methanol. After about 0.5 hour, ether was added to the flask and the flask swirled. The resulting precipitate was filtered under suction, washed well with cold ether and dried, yielding about 4 gm of the respective diphenyl ether potassium salts.

EXAMPLE 10:

Preparation of Methyl-3-(5-(2-chloro-4-(trifluoromethyl)phenoxy)-2-nitro-phenylamino)-3-methylpropionate To a mixture of methyl 3-amino butyrate hydrochloride (15 gm, 0.098 mol) and 4-(2-chloro-4-(trifluoromethyl)phenoxy)-1,2-dinitrobenzene (4.66 gm, 0.013 mol) in 100 ml of dry dioxane there was added 7.1 gm (0.051 mol) of anhydrous potassium carbonate. The suspension was stirred and heated at reflux for 4 hours, cooled to room temperature and poured into water. The solution was extracted with ether and the ether layer isolated, washed with saturated sodium chloride and dried over anhydrous magnesium sulfate. Evaporation under reduced pressure gave an oil which solidified when treated with methanol. Recrystallization from methanol gave a solid of the desired product.

EXAMPLE 11:

Preparation of Methyl-3-(5-(2-chloro-4-(trifluoromethyl)phenoxy)-2-nitro-phenylamino)-2-methylpropionate To a mixture of methyl-2-aminomethyl propionate hydrochloride (5 gm, 0.033 mol), and 4-(2-chloro-4-(trifluoromethyl)phenoxy)-1,2-dinitrobenzene (4.1 gm, 0.011 mol) in 100 ml of dry dioxane there was added 4.5 gm (0.033 mol) of anhydrous potassium carbonate. The solution was stirred at room temperature for about 24 hours, then heated 30 minutes at reflux. The resultant bright-yellow suspension was poured into water, extracted with ether and the ethered solution was isolated, washed with saturated sodium chloride solution, dried over anhydrous magnesium sulfate, filtered and the filtrate evaporated yielding a dard oil. The oil was further evaporated yielding a dard oil. The oil was further purified by filtration through silica gel 60 using 40% ether and 60% hexane as the eluant.

The compounds of examples 2, 4, 6, 12 and 13 were prepared in an analogous manner to examples 1, 4, 7, 10 and 11.

EXAMPLE 15:

Using the procedure described below, diphenyl ethers of the invention were evaluated for control of the following weeds:

Monocots barnyardgrass (*Echinochloa crusgalli*)
downy brome (*Bromus tectorum*)
foxtail (*Setaria viridis*)
Johnsongrass (*Sorghum halepense*)
nutsedge (*Cyperus esculentus*)
quackgrass (*Agropyron repens*)
wild oats (*Avena fatua*)

Dicots cocklebur (*Xanthium pensylvanicum*)
marigold (Tagetes spp.)
morningglory (Ipomoea spp.)
sicklepod (*Cassia obtusifolia*)
tomato (*Lycopersicon esculentum*)
velvetleaf (*Abutilon theophrasti*)

The following test procedure was employed. Seeds of selected crops and weeds were planted in soil in flats. For preemergence tests, the flats were treated with the test compound immediately after the planting. For postemergence tests, the seeds were allowed to germinate, and after two weeks the flats were treated with the test compound. The compounds to be evaluated were dissolved in acetone, diluted with water, and sprayed over the flats using a carrier volume equivalent to 50 gallons weeks after the application of the test compound, the state of growth of the plants was observed and the phytotoxic effect of the compound was evaluated. Table 2 gives the average percent control against the aforementioned monocots (AM) and dicots (AD) achieved by the test compounds, 0=no control and 100=100% control (complete kill).

TABLE 2

| Compound | Rate lb/A | Preemergence AD | Preemergence AM | Postemergence AD | Postemergence AM |
|---|---|---|---|---|---|
| 1 | 0.5 | 100 | 81 | 95 | 18 |
| 2 | 0.5 | 100 | 47 | 96 | 38 |
| 3 | 0.5 | 87 | 45 | 53 | 6 |
| 4 | 0.5 | 99 | 56 | 100 | 31 |
| 5 | 0.5 | 100 | 64 | 100 | 65 |
| 6 | 0.5 | 100 | 60 | 93 | 18 |
| 7 | 0.5 | 100 | 57 | 99 | 28 |
| 8 | 0.5 | 83 | 32 | 78 | 46 |
| 9 | 0.5 | 96 | 53 | 75 | 22 |
| 10 | 0.5 | 87 | 70 | 100 | 79 |
| 11 | 0.5 | 91 | 66 | 100 | 73 |
| 12 | 0.5 | 93 | 64 | 100 | 51 |
| 13 | 0.5 | 80 | 28 | 98 | 36 |
| 14 | 0.5 | 76 | 28 | 80 | 18 |

I claim:

1. A compound of the formula

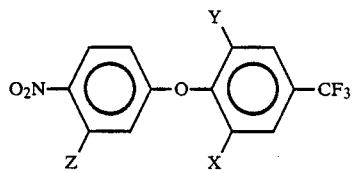

wherein X is a hydrogen, fluoro, chloro, bromo, trifluoromethyl or cyano group; Y is a hydrogen, fluoro, chloro or bromo atom; and Z is NH—$R_1$-$R_2$ wherein $R^1$ is a ($C_2$-$C_5$)alkylene, which may be optionally substituted with methyl groups, and $R^2$ is a carb-($C_1$-$C_4$)alkoxy, a carboxy or an agronomically acceptable salt thereof or a cyano group.

2. A compound of the formula

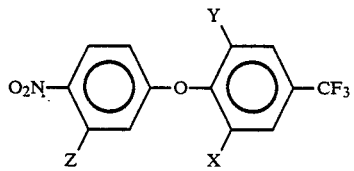

wherein X is fluoro, chloro, bromo, trifluoromethyl or cyano; Y is hydrogen, fluoro, chloro or bromo; and Z is —NH—$R^1$-$R^2$ wherein $R^1$ is a ($C_2$-$C_5$)alkylene, which may be optionally substituted with methyl groups, and $R^2$ is a carb($C_1$-$C_4$)alkoxy, a carboxy or an agronomically acceptable salt thereof or a cyano group.

3. The compound of claim 1 wherein X is a fluoro, chloro or cyano group; Y is a hydrogen, fluoro or chloro atom; $R^1$ is a ($C_2$-$C_5$)alkylene which is optionally substituted with up to one methyl group per carbon atom; and $R^2$ is a carb($C_1$-$C_4$)alkoxy or a carboxy group or an agronomically acceptable salt thereof.

4. The compound of claim 3 wherein X is a fluoro or chloro atom; Y is a hydrogen; $R^1$ is a ($C_2$-$C_3$)alkylene which is optionally substituted with up to one methyl group per carbon atom of the alkylene group or a ($C_4$-$C_5$)alkylene which is substituted with at least one methyl group and optionally substituted with additional methyl groups of up to one per carbon atom of the alkylene group; and $R^2$ is a carb($C_1$-$C_2$)alkoxy or an agronomically acceptable salt thereof.

5. A compound of the formula

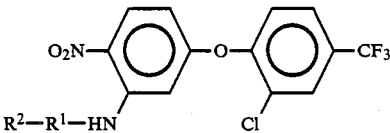

wherein $R^1$ is a ($C_2$-$C_3$)alkylene which is optionally substituted with up to one methyl group per carbon atom of the alkylene group and $R^2$ is a carb($C_1$-$C_2$)alkoxy or agronomically acceptable salts thereof.

6. The compound of claim 5 selected from the group consisting of methyl-3-(5-(2-chloro-4-(trifluoromethyl)phenoxy)-2-nitro-phenylamino)butyrate; methyl-3-(5-(2-chloro-4-(trifluoromethyl)phenoxy)-2-nitro-phenylamino)-2-methylpropionate; ethyl-3-(5-(2-chloro-4-(trifluoromethyl)phenoxy)-2-nitro-phenylamino)propionate; methyl-3-(5-(2-chloro-4-(trifluoromethyl)phenoxy)-2-nitro-phenylamino)propionate; and ethyl-3-(5-(2-chloro-4-(trifluoromethyl)phenoxy)-2-nitro-phenylamino)butyrate.

7. The compound of claim 6 selected from the group consisting of ethyl-3-(5-(2-chloro-4-(trifluoromethyl)phenoxy)-2-nitro-phenylamino)propionate; methyl-3-(5-(2-chloro-4-(trifluoromethyl)phenoxy)-2-nitro-phenylamino)-propionate; and methyl-3-(5-(2-chloro-4-(trifluoromethyl)phenoxy)-2-nitro-phenylamino)butyrate.

8. The compound of claim 7 which is ethyl-3-(5-(2-chloro-4-(trifluoromethyl)phenoxy)-2-nitro-phenylamino)-propionate.

9. The compound of claim 7 which is methyl-3-(5-(2-chloro-4-(trifluoromethyl)phenoxy)-2-nitro-phenylamino)butyrate.

10. A compound of the formula:

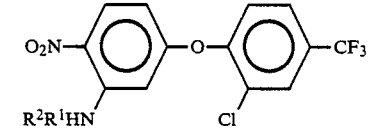

wherein $R^1$ is a ($C_4$-$C_5$)alkylene optionally substituted with additional methyl groups of up to one per carbon atom of the alkylene group; and $R^2$ is a carb($C_1$-$C_2$)alkoxy or a carboxy group or an agronomically acceptable salt thereof.

11. The compound of claim 10 wherein the ($C_4$-$C_5$)-alkylene of $R^1$ is substituted with at least one methyl group and is optionally substituted with additional methyl groups of up to one per carbon atom of the alkylene group.

12. The compound of claim 11 which is methyl-6-(5-(2-chloro-4-(trifluoromethyl)phenoxy)-2-nitro-phenylamino)-hexanoate.

13. A herbicidal composition comprising a herbicidally effective amount of the compound of claim 1 and an agronomically acceptable carrier.

14. A method of controlling weeds which comprises applying to weed seedlings the compound of claim 1 in an amount sufficient to control the growth of the weeds.

15. A method of controlling weeds which comprises applying to weed seedlings the compound of claim 5 in an amount sufficient to control the growth of the weeds.

16. A method of controlling weeds which comprises applying to weed seedlings the compound of claim 10 in an amount sufficient to control the growth of the weeds.

* * * * *